US009629880B2

(12) United States Patent
Watanabe et al.

(10) Patent No.: US 9,629,880 B2
(45) Date of Patent: Apr. 25, 2017

(54) METHOD FOR PRODUCING OYSTER MEAT ESSENCE CONTAINING LARGE AMOUNT OF ANTIOXIDANTS HAVING HIGH ANTIOXIDATIVE POWER AND HIGH ORAC VALUE

(75) Inventors: Mitsugu Watanabe, Tokyo (JP); Takayuki Watanabe, Tokyo (JP); Hideaki Watanabe, Tokyo (JP)

(73) Assignee: Watanable Oyster Laboratory Co., Ltd., Tokyo (JP)

( * ) Notice: Subject to any disclaimer, the term of this patent is extended or adjusted under 35 U.S.C. 154(b) by 239 days.

(21) Appl. No.: 14/003,052

(22) PCT Filed: Sep. 15, 2011

(86) PCT No.: PCT/JP2011/005213
§ 371 (c)(1),
(2), (4) Date: Sep. 4, 2013

(87) PCT Pub. No.: WO2012/140705
PCT Pub. Date: Oct. 18, 2012

(65) Prior Publication Data
US 2013/0337079 A1    Dec. 19, 2013

(30) Foreign Application Priority Data

Apr. 11, 2011   (JP) ................................. 2011-087251
Sep. 6, 2011    (JP) ................................. 2011-193754

(51) Int. Cl.
A61K 35/56    (2015.01)
A61K 35/34    (2015.01)
A61K 35/12    (2015.01)
A61K 35/618   (2015.01)
A23L 33/10    (2016.01)
A23L 17/20    (2016.01)

(52) U.S. Cl.
CPC ............ *A61K 35/618* (2013.01); *A23L 17/20* (2016.08); *A23L 33/10* (2016.08); *A23V 2002/00* (2013.01)

(58) Field of Classification Search
None
See application file for complete search history.

(56) References Cited

U.S. PATENT DOCUMENTS 5,925,382 A * 7/1999 Nomura ................. A23L 3/3472
424/520

FOREIGN PATENT DOCUMENTS

| EP | 0 806 465 | | 11/1997 |
| JP | 61010515 A | * | 1/1986 |
| JP | 10-36275 | | 2/1998 |
| JP | 10-136946 | | 5/1998 |
| JP | 10-136947 | | 5/1998 |
| JP | 2009-22166 | | 2/2009 |
| JP | 2009022166 A | * | 2/2009 |
| JP | 2009-60869 | | 3/2009 |

OTHER PUBLICATIONS

International Search Report issued Dec. 13, 2011 in International (PCT) Application No. PCT/JP2011/005213.
Machine Translation of JP 2009-022166 previously cited in an IDS filed on Sep. 4, 2013.
Machine Translation of JP 2009-60869 previously cited in an IDS filed on Sep. 4, 2013.
Machine Translation of JP 10-136946 previously cited in an IDS filed on Sep. 4, 2013.
Machine Translation of JP 10-136947 previously cited in an IDS filed on Sep. 4, 2013.

* cited by examiner

*Primary Examiner* — Chris R Tate
*Assistant Examiner* — Russell Fiebig
(74) *Attorney, Agent, or Firm* — Wenderoth, Lind & Ponack, L.L.P.

(57) ABSTRACT

To provide a method for producing an oyster meat essence that more amply incorporates an antioxidant substance with high ORAC value as follows. A portion of an oyster meat extract more amply incorporating an antioxidant substance with high ORAC value is selected. An extraction method that allows incorporating further large amount of antioxidant substance with high ORAC value is employed. The beneficial oyster meat extract can be efficiently extracted in large amounts.

Object
An oyster meat is stored in an extraction container where water is accumulated. An oyster meat essence is extracted to generate an extract liquid. The extract liquid is injected to a centrifuge, and concurrently the centrifuge is rotated at a centrifugal acceleration where an antioxidant substance with high antioxidative potency and ORAC value is separated and removed from the extract liquid. The antioxidant substance with higher antioxidative potency and ORAC value is separated. Thus, the oyster meat essence incorporating a large amount of antioxidant substance with high antioxidative potency and ORAC value is obtained.

3 Claims, 12 Drawing Sheets

Fig.5

CALCULATION METHOD OF ORAC VALUE $$ORAC = \frac{netAUC_{Sample}}{netAUC_{Trolox}} \times \frac{[Trolox]}{[Sample]}$$

net AUCSample= AUCSample -AUCBlank
net AUCTolox=AUCTolox- AUCBlank
[Trolox]:Trolox CONCENTRATION($\mu$ mol/L)
[Sample]:Sample CONCENTRATION (g/L)

APPARATUS, REAGENT, AND UNIT USED FOR ORAC METHOD

ANALYZER
    FLUORESCENCE PLATE READER

RADICAL GENERATOR
    AAPH(2,2'-azo-bis(2-amidinopropane)dihydrochloride) OR SIMILAR REACTIVE OXYGEN SPECIES
    Peroxyl radical OR SIMILAR LABELED SUBSTANCE
    Fluorescein(3'6'-dihydroxyspiro[isobenzofuran
    −1[3H],9'[9H]-xanthen]-3-one)

STANDARD SUBSTANCE
    Trolox® (6-hydroxy-2,,5,7,8-tetramethylchroman −2-carboxylicacid)

EXAMPLE OF UNIT
    $\mu$ mol Trolox equibalent / g

Fig. 7

GENERALLY, TO PERFORM CENTRIFUGATION, A "RELATIVE CENTRIFUGAL ACCELERATION" (RCF: Relative Centrifugal Force), WHICH IS EXPRESSED BY THE RATIO WITH THE GRAVITATIONAL ACCELERATION OF THE EARTH, IS USED AS A UNIT OF CENTRIFUGAL ACCELERATION. THE RELATIVE CENTRIFUGAL ACCELERATION IS USUALLY EXPRESSED WITH "G", "xg", OR SIMILER SYMBOL.

HERE, ASSUME THAT THE PARTICLES ROTATE N TIMES PER MINUTE PLACING THE ROTATION AXIS AS THE CENTER: $\omega = 2\pi N/60 (rad/s)$ AND THE GRAVITATIONAL ACCELERATION OF THE EARTH = $980.665 (cm/s^2)$ ARE FOUND. ACCORDINGLY, THE RELATIVE CENTRIFUGAL ACCELERATION RCF IS FOUND BY THE FOLLOWING.

$$RCF = \frac{CENTRIFUGAL\ ACCELERATION}{GRAVITATIONAL\ ACCELERATION\ OF\ EARTH} = r \cdot \left(\frac{2\pi N}{60}\right)^2 \cdot \frac{1}{980.665}$$

THIS EXPRESSION CAN BE SIMPLIFIED AS THE FOLLOWING EXPRESSION.

$$RCF = 1118 \times r \times N^2 \times 10^{-8} \quad (\times g) \quad \cdots\cdots\cdots\cdots\cdots\cdots\cdots\cdots\cdots\cdots\cdots\cdots\cdots (1)$$

r  : ROTATION RADIUS (cm)
    N  : ROTATION SPEED PER MINUTE (rpm)

WHEN "CENTRIFUGAL ACCELERATION" IS SIMPLY REFERRED IN CENTRIFUGATION, THE "CENTRIFUGAL ACCELERATION" IS USUALLY REFERRED TO AS THE "RELATIVE CENTRIFUGAL ACCELERATION".

[CALCULATION EXAMPLE OF MAXIMUM CENTRIFUGAL ACCELERATION]

THE MAXIMUM CENTRIFUGAL ACCELERATION IS CALCULATED FROM THE MAXIMUM ROTATION RADIUS AND THE MAXIMUM ROTATION SPEED OF EACH CENTRIFUGE.

MAXIMUM ROTATION RADIUS   : $r_{max}$ = 11.4 (cm)
    MAXIMUM ROTATION SPEED    : $N_{max}$ = 8000 (rpm)

IF THE CENTRIFUGE SATISFIES THE ABOVE, THE MAXIMUM CENTRIFUGAL ACCELERATION RCFMAX IS AS FOLLOWS FROM THE EXPRESSION (1).

$$RCF_{max} = 1118 \times 11.4 \times (8000)^2 \times 10^{-8} = 8156.928 (\times g)$$

THAT IS, THE MAXIMUM CENTRIFUGAL ACCELERATION OF THE CENTRIFUGE IS CALCULATED AS 8156.928×g. THIS MEANS THAT THE CENTRIFUGE CAN GENERATE THE CENTRIFUGAL ACCELERATION OF EQUAL TO OR MORE THAN 8000 TIMES THE GRAVITATIONAL ACCELERATION.

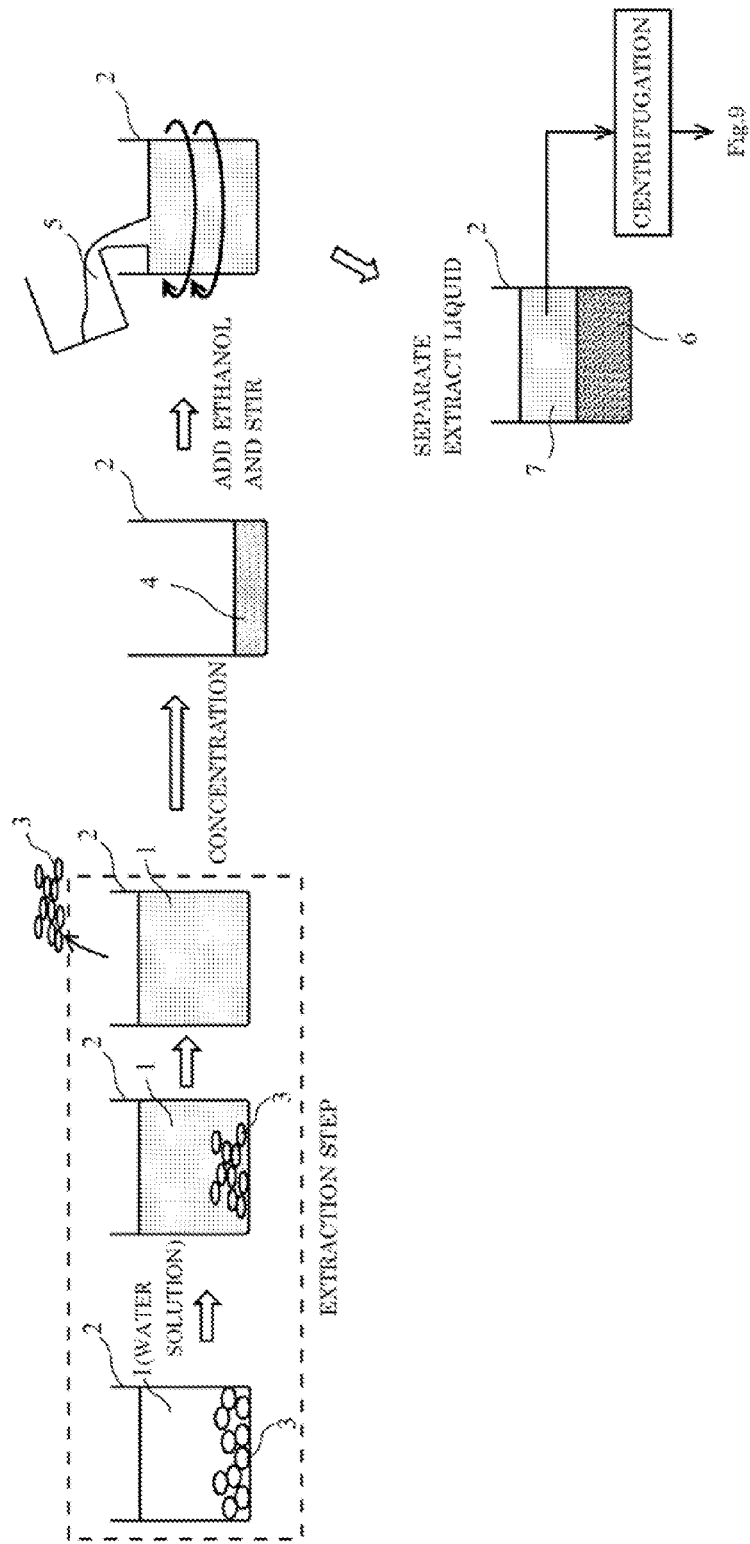

METHOD FOR PRODUCING OYSTER MEAT ESSENCE CONTAINING LARGE AMOUNT OF ANTIOXIDANTS HAVING HIGH ANTIOXIDATIVE POWER AND HIGH ORAC VALUE

TECHNICAL FIELD

The present invention relates to a method for producing an oyster meat essence that incorporates a large amount of antioxidant substance with a high antioxidative potency and ORAC value. The method efficiently extracts an essence of an oyster meat including a large amount of antioxidant substance with a high antioxidative potency and ORAC value, for example, from an oyster meat such as a raw oyster. The antioxidant substance can be extracted to incorporate, without loss, a large amount of the antioxidant substance, present in the oyster meat essence, having a high antioxidative potency and ORAC value.

BACKGROUND ART

Recently, recognition that an essence of an oyster meat is an extremely superior product including many beneficial substances as a dietary supplement product is growing day by day.

Currently, for example, a dietary supplement product or similar product regarding an oyster meat essence extracted by a wide variety of extraction methods has come to be sold (Patent document 1).

Especially, among minerals, whose insufficient dietary intake has become a problem, trace elements of taurine, zinc, and selenium are indispensable for humans, but is prone to being missed. Accordingly, taking in an appropriate amount of the minerals in daily living habits is desired.

Diabetes is a disease that weakens an action of "insulin", which is a hormone reducing a blood sugar, and abnormally increases sugar content in blood due to insufficient insulin. Minerals, such as zinc and selenium, help "action of blood sugar reduction" performed by this insulin. As these minerals are said to "have an insulin action", it is recognized that actually replenishing these minerals to a diabetes patient reduces the blood-sugar level of the diabetes patient. The oyster meat incorporates a large amount of these active ingredients.

To extract the essence of the oyster meat incorporating a large amount of the active ingredient, the following is desired. The oyster meat essence that richly incorporates human body-friendly minerals such as zinc and selenium required for the human body nowadays and beneficial substances, for example, vitamin, taurine, glycogen, and protein in a balanced manner is efficiently extracted. Additionally, a good oyster meat essence is produced. The inventors have continuously invented methods for producing the oyster meat essence satisfying these requirements and obtained patents on the method.

Recently, it has been confirmed that the oyster meat also incorporates a large amount of antioxidant substance with a so-called high antioxidative property, which has recently attracted attention. The inventors of the present invention further clarify the above-described matters through various studies and experiments by the inventors of the present invention. Especially, development of a method for producing an oyster meat essence that more amply incorporates a large amount of antioxidant substance with a high antioxidative potency and ORAC value has been strongly desired.

Especially, the inventors of the present invention have recently been studying on the portion of the oyster meat including a large amount of the antioxidant substance with a high antioxidative potency and ORAC value, and the method for extracting the oyster meat essence that incorporates a large amount of antioxidant substance with a high antioxidative potency and ORAC value. The inventors have been conducting inventive and creative activities regarding the production method where an oyster meat extract incorporating a large amount of antioxidant substance with a high antioxidative potency and ORAC value can be efficiently extracted, that is, the production method where the oyster meat essence incorporating a large amount of antioxidant substance with a high antioxidative potency and ORAC value can be appropriately extracted and produced.

So-called reactive oxygen is generated by aerobic life and causes oxidation of lipid, protein, and nucleic acid, thus damaging a cell. Usually, the oxidation level of a living body is maintained substantially constant by a balance between a reactive oxygen producing system and a scavenging system using an antioxidant substance. The balance is lost due to various factors such as drugs, radiation, ischemia, or similar cause. An inclination to the reactive oxygen producing system is referred to as oxidant stress.

It is considered that accumulation of this oxidant stress is one cause of various diseases such as cancer, arteriosclerotic disease, an ischemia/reperfusion injury, chronic rheumatoid arthritis, diabetes, a neurological disorder such as an Alzheimer's disease and a Parkinson's disease; and aging.

An oyster, for example, Crassostreagigas is a bivalve belonging to a family Ostreidae in the order Pterioida. The habitat covers the entire East Asia region including Japan. Nowadays, the Crassostreagigas is also cultivated in France and Australia, and is renowned as the most eaten oyster in the world. Since it is highly nutritious, the oyster has been used for food since ancient times. As described above, the oyster meat essence extracted from the oyster meat includes a large amount of minerals such as calcium, zinc, selenium, copper, manganese, or similar material as well as glycogen and protein. Furthermore, the oyster meat essence incorporates the large amount of the antioxidant substance with the high antioxidative potency and ORAC value.

As a value indicating the extent of the antioxidative potency, a so-called ORAC value is generally used. The ORAC value, for example, is said to be a value extremely frequently used for food product and supplement typically in the United States of America. In other words, the ORAC value is a value of "Oxygen Radical Absorbance Capacity". The ORAC value is an index made by analyzing, and converting into a numerical value, to what extent a food product or supplement has "the power to absorb reactive oxygen (antioxidative potency)." That is why the ORAC value is said to be a value indicating strength of antioxidative potency.

The reactive oxygen is one kind of so-called free radical and is generated when oxygen is taken up by respiration. If the reactive oxygen in a body increases too much due to illumination with ultraviolet light, stress, smoking, or similar cause, the cell is damaged. This is said to be a cause of wrinkles, liver spots, and other aging, and a cause of lifestyle-related disease such as diabetes.

Daily taking in a food product with a high antioxidative potency or similar product is a key to remove reactive oxygen, which is a cause of aging.

The "ORAC value" is a reference for taking in the food product with a high antioxidative potency. The higher the value, the higher the antioxidative potency is. Taking the food product with the high ORAC value allows protection from aging and a disease.

[Patent document 1] Japanese Unexamined Patent Application Publication No. H10-136946

DISCLOSURE OF THE INVENTION

Problems to be Solved by the Invention

The present invention has been made to satisfy the conventional requirements. One of its objectives is to provide a method for producing an oyster meat essence that incorporates a large amount of antioxidant substance with a high ORAC value as follows. A portion of an oyster meat extract more amply incorporating antioxidant substance with so-called high antioxidative potency, namely, high ORAC value, is selected. An extraction method that allows more amply incorporating antioxidant substance with a high ORAC value in the selected extract is employed. The beneficial oyster meat extract that incorporates the antioxidant substance with extremely high ORAC value can be efficiently extracted in large amounts. The oyster meat incorporating a large amount of antioxidant substance with a high ORAC value can be produced.

Means for Solving the Problem

A method for producing an oyster meat essence that incorporates a large amount of antioxidant substance with high antioxidative potency and ORAC value according to the present invention includes: storing an oyster meat in an extraction container where water is accumulated, extracting an oyster meat essence from the oyster meat in the extraction container to generate an extract liquid, injecting the generated extract liquid to a centrifuge, concurrently rotating the centrifuge at a centrifugal acceleration so that an antioxidant substance with high antioxidative potency and ORAC value is separated and removed from the extract liquid so as to separate the antioxidant substance with high antioxidative potency and ORAC value from the liquid, and obtaining the oyster meat essence incorporating the large amount of antioxidant substance with high antioxidative potency and ORAC value after the separation.

Or, a method for producing an oyster meat essence that incorporates a large amount of antioxidant substance with high antioxidative potency and ORAC value according to the present invention includes: storing an oyster meat in an extraction container where water is accumulated, extracting an oyster meat essence from the oyster meat in the extraction container to generate an extract liquid, removing the oyster meat after the extraction, concentrating the extract liquid after the removal of the oyster meat to generate a concentration liquid, adding ethanol to the concentration liquid, stirring the concentration liquid to separate the concentration liquid into a precipitate and a supernatant, removing the supernatant after the separation, injecting the removed supernatant to a centrifuge, concurrently rotating the centrifuge at a centrifugal acceleration so that an antioxidant substance with high antioxidative potency and ORAC value in the supernatant is separated and removed, separating the antioxidant substance with high antioxidative potency and ORAC value as a centrifugation supernatant from the injected supernatant, and collecting the oyster meat essence incorporating the large amount of antioxidant substance with high antioxidative potency and ORAC value in the centrifugation supernatant.

Or, a method for producing an oyster meat essence that incorporates a large amount of antioxidant substance with high antioxidative potency and ORAC value according to the present invention includes: storing an oyster meat in an extraction container where water is accumulated, extracting an oyster meat essence from the oyster meat in the extraction container to generate an extract liquid, removing the oyster meat after the extraction, concentrating the extract liquid after the removal of the oyster meat to generate a concentration liquid, adding ethanol to the concentration liquid, stirring the concentration liquid to separate the concentration liquid into a precipitate and a supernatant, removing the supernatant after the separation, injecting the removed supernatant to a centrifuge, concurrently rotating the centrifuge at a rotation speed where a centrifugal acceleration exceeding a diffusion force of a substance without antioxidative potency or a substance with low antioxidative potency in the supernatant is allowed to be obtained, separating the substance without antioxidative potency or the substance with low antioxidative potency from the injected supernatant to a centrifugation precipitate side to separate the supernatant into a centrifugation supernatant and a centrifugation precipitate, and incorporating a large amount of antioxidant substance with high antioxidative potency and ORAC value in the centrifugation supernatant after the separation.

Or, a method for producing an oyster meat essence that incorporates a large amount of antioxidant substance with high antioxidative potency and ORAC value according to the present invention includes: storing an oyster meat in an extraction container where water is accumulated, extracting an oyster meat essence from the oyster meat in the extraction container to generate an extract liquid, removing the oyster meat after the extraction, concentrating the extract liquid after the removal of the oyster meat to generate a concentration liquid, adding ethanol to the concentration liquid, stirring the concentration liquid to separate the concentration liquid into a precipitate and a supernatant, removing the supernatant after the separation, injecting the removed supernatant continuously to a continuous centrifuge, concurrently rotating the continuous centrifuge at a rotation speed where a centrifugal acceleration exceeding a diffusion force of a substance without antioxidative potency or a substance with low antioxidative potency in the supernatant is allowed to be obtained, separating the substance without antioxidative potency or the substance with low antioxidative potency from the injected supernatant to a centrifugation precipitate side to separate the supernatant into a centrifugation supernatant and a centrifugation precipitate, and incorporating a large amount of antioxidant substance with high antioxidative potency and ORAC value in the centrifugation supernatant after the separation.

Or, a method for producing an oyster meat essence that incorporates a large amount of antioxidant substance with high antioxidative potency and ORAC value according to the present invention includes: storing an oyster meat in an extraction container where water is accumulated, extracting an oyster meat essence from the oyster meat in the extraction container to generate an extract liquid, removing the oyster meat after the extraction, concentrating the extract liquid after the removal of the oyster meat to generate concentration liquid, adding ethanol to the concentration liquid so that ethanol concentration becomes 30% to 90%, preferably, 70%, stirring the concentration liquid to separate the concentration liquid into a precipitate and a supernatant, removing the supernatant after the separation, injecting the removed supernatant continuously to a continuous centrifuge, concurrently rotating the continuous centrifuge at a rotation speed where a centrifugal acceleration exceeding a diffusion force of a substance without antioxidative potency or a substance with low antioxidative potency in the supernatant is able to be obtained, separating the substance without antioxidative potency or the substance with low antioxidative potency from the injected supernatant to a centrifugation precipitate side to separate the supernatant into a centrifugation supernatant and a centrifugation precipitate, and incorporating a large amount of antioxidant substance with high antioxidative potency and ORAC value in the centrifugation supernatant after the separation.

Or, the method for producing an oyster meat essence that incorporates a large amount of antioxidant substance with a high antioxidative potency and ORAC value according to the present invention is configured as follows. A centrifugal acceleration of the continuous centrifuge exceeding the diffusion force of the substance without antioxidative potency or the substance with low antioxidative potency in the supernatant is approximately 8000×G.

Or, a method for producing an oyster meat essence that incorporates a large amount of antioxidant substance with a high ORAC value according to the present invention includes: storing an oyster meat in an extraction container where water is accumulated, extracting an oyster meat essence from the oyster meat in the extraction container to generate an extract liquid, subsequently concentrating the extract liquid to generate a first concentration liquid, adding ethanol to the first concentration liquid, separating the first concentration liquid into a precipitate and a first supernatant, removing the first supernatant after the separation, centrifuging the first supernatant to separate the first supernatant into a precipitate and a second supernatant, concentrating the separated second supernatant to generate a second concentration liquid, adding ethanol to the second concentration liquid and shaking the second concentration liquid, separating the second concentration liquid into a third supernatant of an ethanol layer at an upper side and a water layer at a lower side to incorporate a large amount of antioxidant substance with high ORAC value in the separated third supernatant.

Or, a method for producing an oyster meat essence that incorporates a large amount of antioxidant substance with high ORAC value according to the present invention includes: storing an oyster meat in an extraction container where water is accumulated, extracting an oyster meat essence from the oyster meat in the extraction container to generate an extract liquid, subsequently concentrating the extract liquid to generate a first concentration liquid, adding ethanol to the first concentration liquid, separating the first concentration liquid into a precipitate and a first supernatant, removing the first supernatant after the separation, centrifuging the removed first supernatant to separate the first supernatant into a precipitate and a second supernatant, concentrating the separated second supernatant to generate a second concentration liquid, adding ethanol to the second concentration liquid, shaking the second concentration liquid, separating the second concentration liquid into a third supernatant of an ethanol layer at an upper side and a water layer at a lower side, and concentrating the separated third supernatant to generate a paste-like concentrate to incorporate a large amount of antioxidant substance with high ORAC value in the concentrate.

Or, a method for producing an oyster meat essence that incorporates a large amount of antioxidant substance with high ORAC value according to the present invention includes: storing an oyster meat in an extraction container where water is accumulated, extracting an oyster meat essence from the oyster meat in the extraction container to generate an extract liquid, subsequently concentrating the extract liquid to generate a first concentration liquid, adding ethanol to the first concentration liquid, separating the first concentration liquid into a precipitate and a first supernatant, removing the first supernatant after the separation, centrifuging the removed first supernatant to separate the first supernatant into a precipitate and a second supernatant, concentrating the separated second supernatant to generate a second concentration liquid, adding ethanol to the second concentration liquid so that ethanol concentration becomes 30% to 90%, shaking the second concentration liquid, separating the second concentration liquid into a third supernatant of an ethanol layer at an upper side and a water layer at a lower side to incorporate a large amount of hydrophilic antioxidant substance, oleophilic antioxidant substance, and amphiphilic antioxidant substance with high ORAC value in the third supernatant.

Or, a method for producing an oyster meat essence that incorporates a large amount of antioxidant substance with high ORAC value according to the present invention includes: storing an oyster meat in an extraction container where water is accumulated, extracting an oyster meat essence from the oyster meat in the extraction container to generate an extract liquid, subsequently concentrating the extract liquid to generate a first concentration liquid, adding ethanol to the first concentration liquid, separating the first concentration liquid into a precipitate and a first supernatant, removing the first supernatant after the separation, centrifuging the removed first supernatant to separate the first supernatant into a precipitate and a second supernatant, concentrating the separated second supernatant to generate a second concentration liquid, adding ethanol to the second concentration liquid so that ethanol concentration becomes 30% to 90%, shaking the second concentration liquid, separating the second concentration liquid into a third supernatant of an ethanol layer at an upper side and a water layer at a lower side, and concentrating the separated third supernatant to generate a paste-like concentrate to incorporate a large amount of hydrophilic antioxidant substance, oleophilic antioxidant substance, and amphiphilic antioxidant substance with high ORAC value in the concentrate.

Or, the method for producing an oyster meat essence that incorporates a large amount of antioxidant substance with high ORAC value according to the present invention includes: centrifuging the third supernatant to separate the third supernatant into a precipitate and a fourth supernatant, concentrating the separated fourth supernatant to generate a paste-like concentrate to incorporate a large amount of hydrophilic antioxidant substance, oleophilic antioxidant substance, and amphiphilic antioxidant substance with high ORAC value in the concentrate.

Or, the method for producing an oyster meat essence that incorporates a large amount of antioxidant substance with high ORAC value according to the present invention includes: further repeatedly performing the centrifugation to remove a supernatant after a final centrifugation, concentrating the supernatant to generate a paste-like concentrate to incorporate a large amount of hydrophilic antioxidant substance, oleophilic antioxidant substance, and amphiphilic antioxidant substance with high ORAC value in the concentrate.

Advantages of the Invention

The present invention achieves an excellent effect as follows.

An oyster meat that more amply incorporates antioxidant substance with a high ORAC value, in other words, a portion of an oyster meat extract incorporating a large amount of antioxidant substance with a high antioxidative potency, namely, high ORAC value, is selected. An extraction method that allows incorporating a large amount of antioxidant substance with a high ORAC value in the selected extract is applied. The oyster meat extract that incorporates a large amount of the antioxidant substance with a high ORAC value can be efficiently extracted in large amounts. The oyster meat essence incorporating a large amount of antioxidant substance with a high ORAC value can be produced.

BRIEF DESCRIPTION OF DRAWINGS

FIG. 5 is an explanatory view illustrating a calculation method of an ORAC value and an apparatus, a reagent, and a unit used for the ORAC method;

FIG. 7 is an explanatory view illustrating a calculation example of a maximum centrifugal acceleration;

FIG. 8 is an explanatory view of a schematic configuration illustrating a method for producing the oyster meat essence incorporating a large amount of antioxidant substance with a high ORAC value according to a second embodiment of the present invention;

BEST MODE FOR CARRYING OUT THE INVENTION

A preferred embodiment of the present invention will be described below.

Working Example 1

Figure 1:
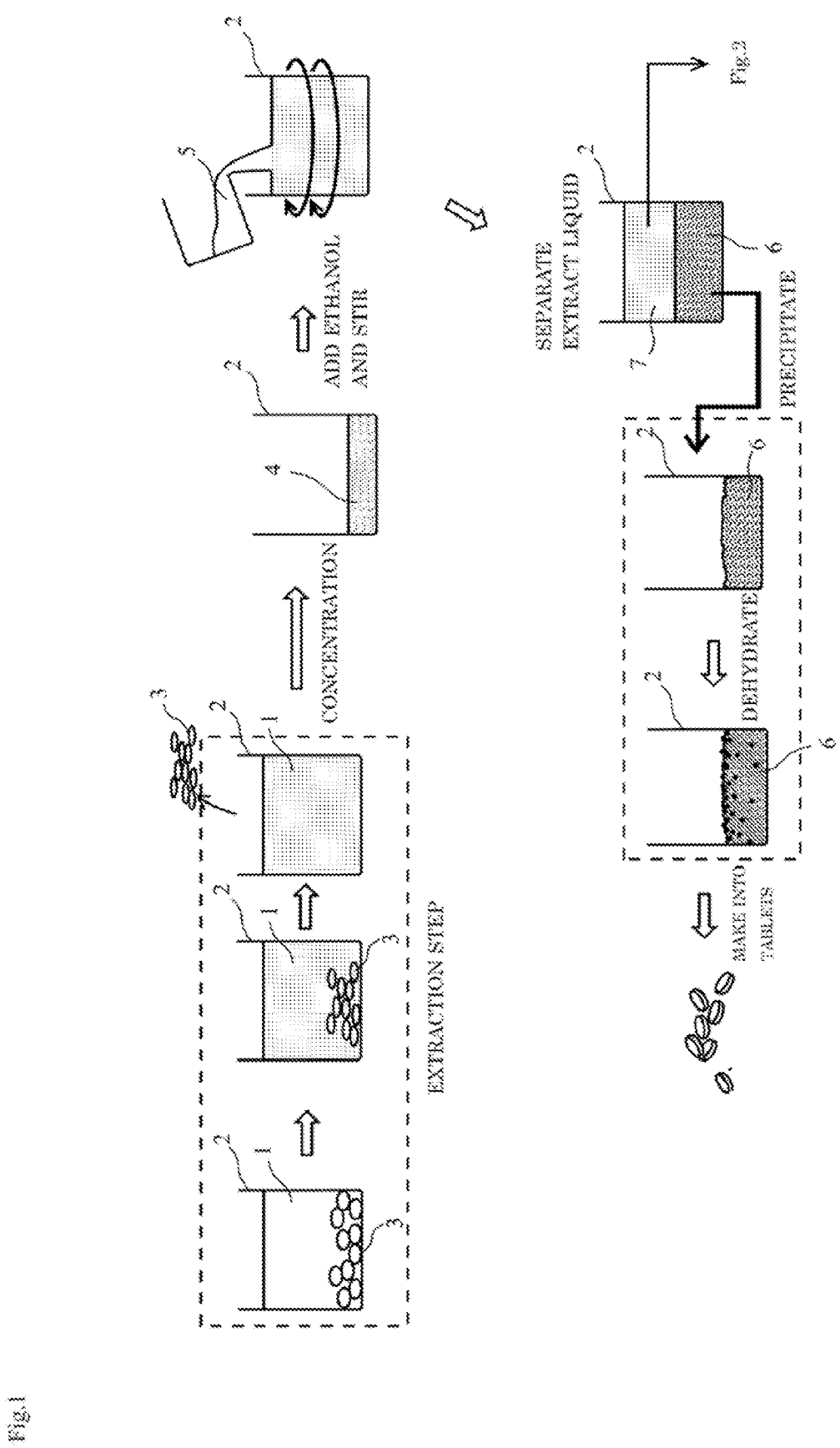
FIG. 1 is an explanatory view of a schematic configuration illustrating a method for producing an oyster meat essence incorporating a large amount of antioxidant substance with a high antioxidative potency and ORAC value according to the present invention (first)

First, as illustrated in FIG. 1, to extract an oyster meat essence, an oyster meat 3 is stored in an extraction container 2 accumulating water 1.

Here, the kind of the water 1 used for the extraction is not limited. Generally, water may be used. The temperature of this water is not also limited. The water may be at a general normal temperature, may be warm water at 30° C. to 50° C., or may be hot water equal to or more than 50° C. Ethanol may be mixed with the water to create an ethanol solution. Mixing ethanol in water promotes the extraction of the oyster meat essence in the ethanol solution.

In the extraction, the inside of the extraction container 2 may be at normal pressure, or the inside of the extraction container 2 may be sealed, and the pressure may be reduced to equal to or less than 1 atmosphere or the pressure may be increased to equal to or more than 1 atmosphere.

This is to select a good extraction method that allows incorporating a large amount of antioxidant substance with a high antioxidative potency.

Next, after a lapse of a predetermined period, for example, after a lapse of extraction period of several hours, the oyster meat 3 is removed from the inside of the extraction container 2, and the extracted extract liquid in the extraction container 2 is concentrated, thus concentration liquid 4 is created.

Various concentration methods are also available for this concentration method. The concentration method is not limited in the present invention, and any concentration method is applicable. A so-called low-temperature heating condensation method and a high-temperature heating condensation method are applicable.

The concentration ratio of the concentration liquid 4 is not also limited. The concentration liquid 4 may be concentrated to one third or half.

Next, ethanol 5 is added to the concentration liquid 4 so that the ethanol concentration may be about 30% to 80%, preferably, the ethanol concentration may be 70%. The concentration liquid 4 where the ethanol 5 has been added and attenuated is stirred and separated into a precipitate 6 and a supernatant 7. This separation method is not limited. However, in a natural separation method by means of natural sedimentation, after the solution is stirred, it is left as it is for a predetermined period of time to await the precipitate 6 precipitating naturally.

After the precipitate 6 precipitates and the precipitate 6 and the supernatant 7 are completely separated, only this supernatant 7 is removed.

Figure 2:
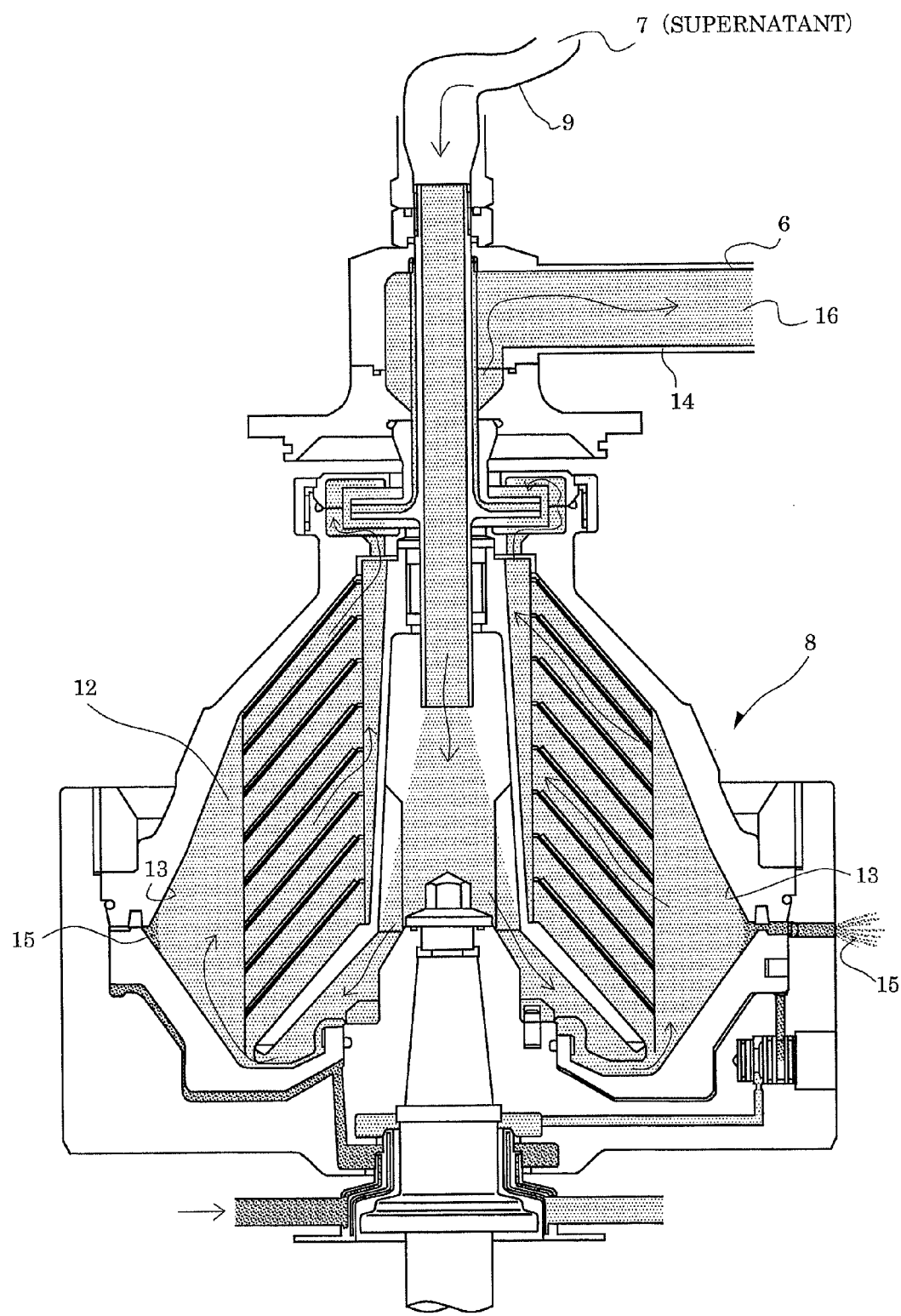
FIG. 2 is an explanatory view illustrating a schematic configuration of a continuous centrifuge according to the present invention.
Figure 3:
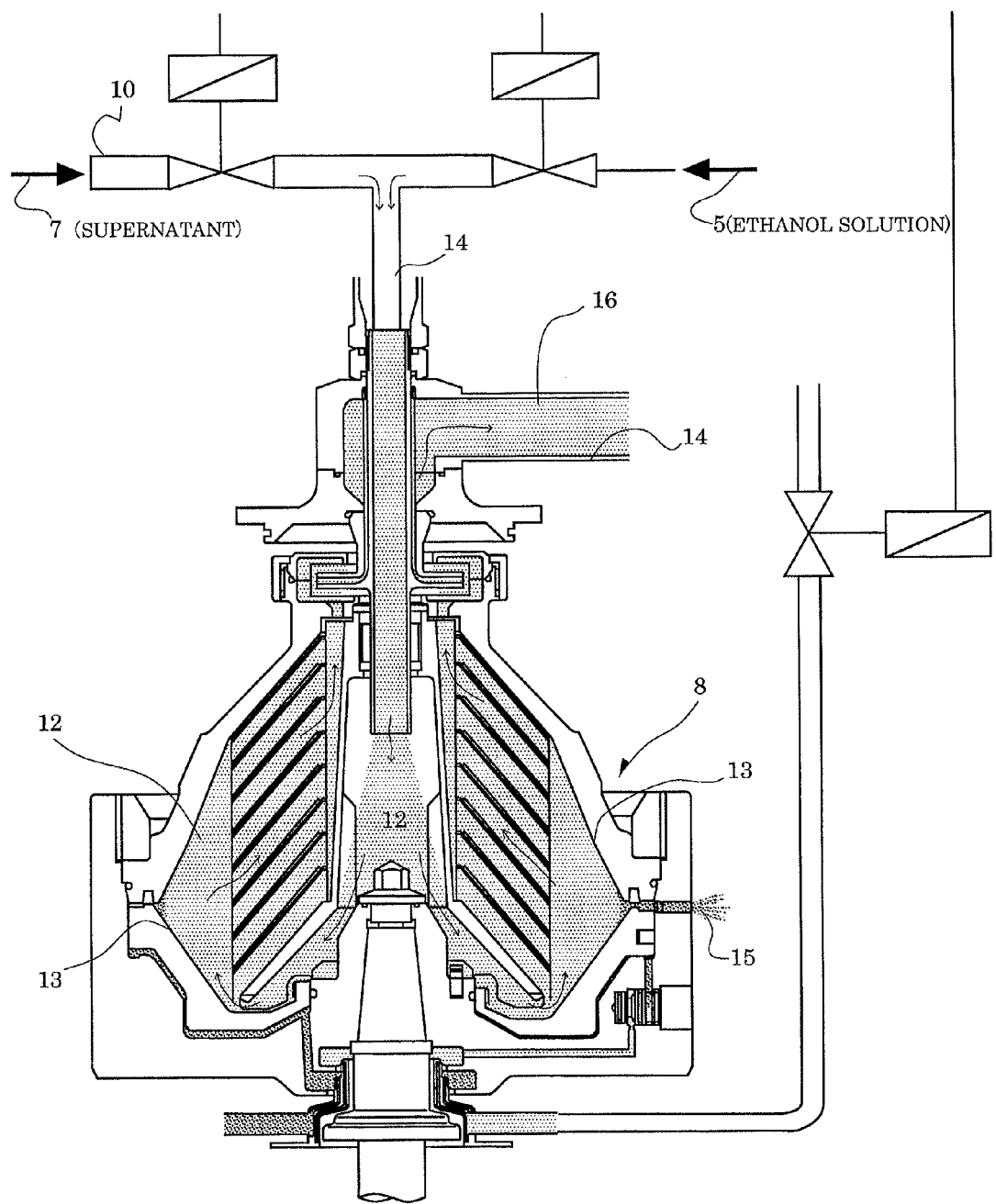
FIG. 3 is an explanatory view illustrating a schematic configuration of the continuous centrifuge according to another embodiment.

It is constituted so that this supernatant 7 can be continuously injected from an injection pipe 9 of a continuous centrifuge 8 illustrated in FIG. 2 to the inside of the continuous centrifuge 8. As shown in FIG. 3, the supernatant 7 may be injected from an injection pipe 10 on the left side while the ethanol 5 may be injected from an injection pipe 11 on the right side. The action of the ethanol 5 promotes the centrifugation action of the continuous centrifuge 8 for further separation.

Here, the injection of the predetermined amount of the supernatant 7 to the inside of the continuous centrifuge 8 is confirmed, and the continuous centrifuge 8 operates. Thus, the supernatant 7 is continuously separated into a so-called centrifugation precipitate 15 and a centrifugation supernatant 16.

As seen from FIG. 2 and FIG. 3, the so-called centrifugation precipitate 15 is collected to an outer periphery sidewall 13 side of a storage tank 12 by a centrifugal force. Apart from that, the so-called centrifugation supernatant 16 is delivered from upward of the storage tank 12 to the outside via a delivery pipe 14.

In this working example, as seen from FIG. 1, for example, the concentration liquid 4 where the ethanol 5 had been added so that the concentration liquid 4 may become the concentration of 70% was stirred, and then it was left to await the concentration liquid 4 to precipitating naturally.

The supernatant 7 extracted after the natural precipitation of, for example, 30 liters, was continuously injected to the continuous centrifuge 8.

The continuous centrifuge 8 was operated, thus centrifugation was continuously performed on the supernatant 7.

As a result, it was confirmed that the so-called centrifugation precipitate 15 of 0.3 liters and the continuous centrifugation supernatant 16 of 29.7 liters were extracted.

In the present invention, it was able to be confirmed that the continuous centrifugation supernatant 16 incorporated a large amount of antioxidant substance with a high antioxidative potency and ORAC value.

Here, to what extent of substances with antioxidative potency were contained in the centrifugation supernatant 16 was examined by a so-called Oxygen Radical Absorbance Capacity method (an ORAC method). By the ORAC method, a value indicating the antioxidative potency, namely, an ORAC value was detected. Consequently, as described above, it was confirmed that the centrifugation supernatant 16 incorporated the antioxidant substance with extremely high antioxidative potency and ORAC value.

Now, the measurement principle of the ORAC method will be somewhat described. First, in the case where constant reactive oxygen species are generated, the fluorescence intensity degraded by the reactive oxygen species is measured, and the curve of the fluorescence intensity decreasing over time is depicted, the rate of decrease in the fluorescence intensity of the fluorescent substance is delayed by coexistence of the antioxidant substance with the reaction system. Accordingly, with this principle, the presence of the antioxidant substance can be confirmed.

Figure 4:
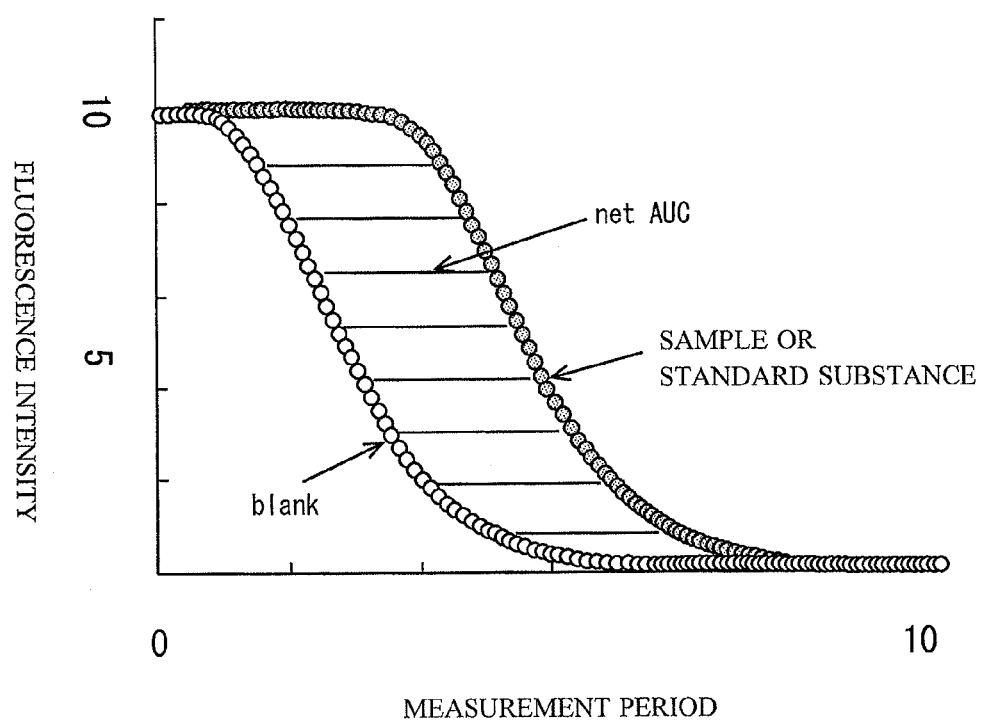
FIG. 4 is an explanatory view illustrating a measurement principle of an ORAC method.

Based on the principles, a description will be given with reference to FIG. 4. The difference between the Area Under the Curve (AUC) of the fluorescence intensity under the presence of a sample or a standard substance, and the AUC under their absence (blank) is calculated (the net AUC). Regarding the net AUC for the sample, a relative value with respect to the net AUC of a standard substance (Trolox) of known concentration to is found. The relative value is as a base converted into Trolox concentration, and taken as the antioxidative potency of the sample (units—µmol TE/g: micromoles Trolox-equivalent/gram).

The calculation method of the ORAC value will be illustrated in FIG. 5.

That is, in the ORAC method, first, a fluorescent probe (Fluorescein) is added to a sample solution or a standard solution (Trolox), and activation oxygen is generated using AAPH (2,2'-Azobis(2-amidinopropane)dihydrochloride) as a radical initiator. This oxidizes the Fluorescein by the reactive oxygen.

Since the oxidized Fluorescein does not exhibit fluorescence, the fluorescence intensity is reduced over time. If the sample exhibits antioxidative potency, the reactive oxygen is removed by the antioxidant substance, and the oxidation of the Fluorescein is suppressed. Accordingly, the fluorescence intensity of the Fluorescein is maintained and the reduction speed is delayed compared with the case where the antioxidant substance is absent (blank).

The fluorescence intensity of the sample or of Trolox, and of the blank are plotted on the vertical axis while the measurement period is plotted on the horizontal axis. The difference between the Area Under the Curve of the fluorescence intensity of the sample solution or of Trolox ("AUCsample" or "AUCTrolox"), and the Area Under the Curve of the blank ("AUCblank"), that is, the area of the diagonal-hatching section, is calculated (each respectively referred to as "netAUCsample" and "netAUCTrolox"). The Trolox concentration equivalent to netAUCsample for the sample is found from netAUCTrolox for the standard substance. The ORAC value is calculated, for example, as the number of micromoles of Trolox per gram of the sample.

Accordingly, for example, µmole TE/g (TE: Trolox-Equivalent) is employed as the unit of the ORAC value.

Here, the ORAC value is expressed by converting the antioxidative potency into the amount of standard substance (Trolox). It should be noted that the ORAC value is not a value indicating a specific weight of antioxidative substance. However, if the ORAC value is high, for example, it can be seen that the oyster meat essence incorporates an antioxidant substance with a high antioxidative potency.

In this working example, the ORAC value of the continuous centrifugation supernatant 16 was detected. The detected value was 160 µmole TE/g, which was extremely high value among usual food groups.

Figure 6:
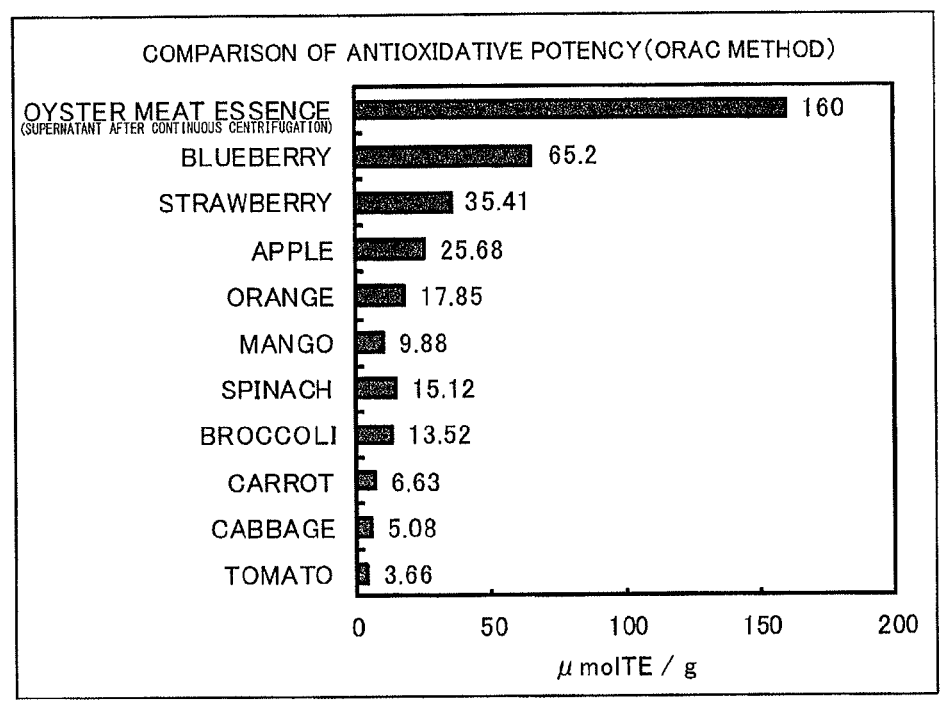
FIG. 6 is an explanatory view illustrating ORAC values of various food products.

ORAC Company in the United States of America makes a database of ORAC values of various food products. The graph of the ORAC values is illustrated in FIG. 6. As seen from FIG. 6, even a blueberry, which is recognized as having a high ORAC value by ORAC Company in the United States of America, the ORAC value is 66.2 µmole TE/g.

In contrast to this, it can be seen that the oyster meat essence of this working example, namely, the continuous centrifugation supernatant 16 incorporates an antioxidant substance with the ORAC value of 160 µmole TE/g, which is a value regarded as having high antioxidative potency and ORAC value approximately double the ORAC value of the blueberry.

The inventors of the present invention added the ethanol 5 to the oyster meat essence before being separated by the continuous centrifuge 8 in the present invention, namely, the concentration liquid 4 of the extract liquid as illustrated in FIG. 1. Then, the ORAC value of the solution, which had become an ethanol solution with a concentration of 70%, for example, was also detected. As a result, the ORAC value of 132 µmole TE/g was detected from the solution that had become the ethanol solution with a concentration of 70%.

As described above, the liquid of 30 liters made as the ethanol solution was centrifuged by the continuous centrifuge 8 as described above to separate the liquid into the centrifugation supernatant 16 of 29.7 liters and the centrifugation precipitate 15 of 0.3 liters. Then, the ORAC value of the continuous centrifugation supernatant 16 indicated a high value, 160 µmole TE/g, as described above. On the contrary, the ORAC value of the continuous centrifugation precipitate 15 indicated 30.7 µmole TE/g.

The reason for this is considered as follows. The continuous centrifuge 8 is rotated with strong rotational force, and centrifugal acceleration of equal to or more than the usual gravitation is applied to the injected supernatant 7.

As a result, forcible separation is performed with the centrifugal acceleration. Accordingly, substances that are never separated and precipitated by the natural precipitation, that is, a substance without the antioxidative potency of the antioxidant substance and a substance with low antioxidative potency are considered to be forcibly separated. These substances are understood to be included in the continuous centrifugation precipitate 15 with the strong centrifugal acceleration.

That is, the centrifugal acceleration by the rotation of the continuous centrifuge 8 exceeds a diffusion force where so-called fine particles, which do not precipitate only by the usual gravitation such as gravitation in natural precipitation, for example, the substance without the antioxidative potency of the antioxidant substance or the substance with low antioxidative potency, try to diffuse. Thus, the substance without the antioxidative potency of the antioxidant substance or the substance with low antioxidative potency, for example, is forcibly separated to the centrifugation precipitate 15 side.

This is because of the following reasons. By operating and rotating the continuous centrifuge 8, the centrifugal acceleration is acted on the supernatant 7 injected in the storage tank 12. When this centrifugal acceleration becomes larger than the diffusion force where, for example, the substance without the antioxidative potency of the antioxidant substance or the substance with low antioxidative potency attempts to diffuses, these substances that do not precipitate in the natural precipitation are also separated. Thus, the centrifugation precipitate 15 is formed.

Accordingly, the ORAC value before separation by the continuous centrifuge, a so-called solution of the concentration liquid where ethanol had been added, was 132 mole TE/g. Meanwhile, the ORAC value of the supernatant generated by forcible separation with the continuous centrifuge was 160 µmole TE/g, which is an extremely high value. This allows extracting, obtaining, and producing an oyster meat essence with a large amount of antioxidant substance with extremely high antioxidative potency.

The rotation speed of the continuous centrifuge 8 where the centrifugal acceleration exceeding the diffusion force of, for example, the substance without the antioxidative potency of the antioxidant substance or the substance with low antioxidative potency present in the supernatant 7 can be obtained will be considered. As seen from FIG. 7, assume that the maximum rotation radius of the continuous centrifuge 8 is 11.4 cm and the maximum rotation speed of the continuous centrifuge 8 is 8000 rpm. Then, the maximum centrifugal acceleration is a value of approximately 8157×g.

Therefore, in the present invention, the maximum centrifugal acceleration of the continuous centrifuge 8 had a value of approximately 8157×g. It has been proved that the centrifugal acceleration around this value exceeds the diffusion force of a hindrance (particle) that inhibits the antioxidative potency of the antioxidant substance present in the supernatant 7.

Working Example 2

Next, the working example 2 according to the present invention will be described with reference to FIG. 8 to FIG. 12. First, to extract an oyster meat essence, the oyster meat 3 is stored in the extraction container 2 accumulating the water 1.

Here, the kind of the water 1 used for the extraction is not limited similarly to the working example 1. Generally, water may be used. The temperature of this water is not also limited. The water may be at a normal temperature, may be warm water around 30° C. to 50° C., or may be hot water equal to or more than 50° C. The ethanol 5 may be mixed with the water to use an ethanol solution. Mixing ethanol in water promotes the extraction of the oyster meat essence in the ethanol solution.

In the extraction, the inside of the extraction container 2 may be at normal pressure, or the inside of the extraction container 2 may be sealed and the pressure may be reduced to equal to or less than 1 atmosphere or the pressure may be increased to equal to or more than 1 atmosphere.

This is to examine and select a method for extracting a substance incorporating a large amount of antioxidant substance with a high antioxidative potency, namely, a high ORAC value described below.

Next, after a lapse of a predetermined period, for example, after a lapse of extraction period of several hours, the oyster meat 3 is removed from the inside of the extraction container 2. After the removal, the extracted extract liquid in the extraction container 2 is concentrated, thus the first concentration liquid 4 is created.

Various concentration methods are also available as the concentration method of this first concentration liquid 4. The concentration method is not limited in the present invention, and any method is applicable. A so-called low-temperature heating condensation method and a high-temperature heating condensation method are applicable.

The concentration ratio of the first concentration liquid 4 is not also limited. The concentration liquid 4 may be concentrated to one third or half.

Next, the ethanol 5 is added to the first concentration liquid 4 so that the ethanol concentration may be about 30% to 90%, preferably, the ethanol concentration may be 70%. Consequently, the first concentration liquid 4 attenuated by the added ethanol 5 is stirred and separated into the precipitate 6 and the first supernatant 7.

This separation method is also not limited. However, in a natural separation method by means of natural sedimentation, after the solution is stirred, it is left as it is for a predetermined period of time to await the precipitate 6 precipitating naturally.

In this working example, the ORAC values of the precipitate 6 and the first supernatant 7 in this step were measured. The ORAC value per gram of the precipitate 6 was only 12.32 µmol TE/g: micromoles Trolox-equivalent/gram. The ORAC value per gram of the first supernatant 7 was 66 µmol TE/g: micromoles Trolox-equivalent/gram.

Thus, it is understood that in the liquid before the centrifugation described below, especially in the precipitate 6, the antioxidant substance with a high ORAC value was not separated. It is also understood that the antioxidant substance with a high ORAC value was not separated to exist in the first supernatant 7.

However, by repeatedly performing the processes such as centrifugation, shaking, and centrifugation on the first supernatant 7, a second, a third, and a fourth supernatants were generated. This allowed extracting an antioxidant substance with a high ORAC value into, for example, the second, the third, and the fourth supernatants.

Here, after the first supernatant 7 is removed, the first supernatant 7 is centrifuged with, for example, the continuous centrifuge to separate the first supernatant 7 into the precipitate 6 and a second supernatant 17.

Figures 9, 10:
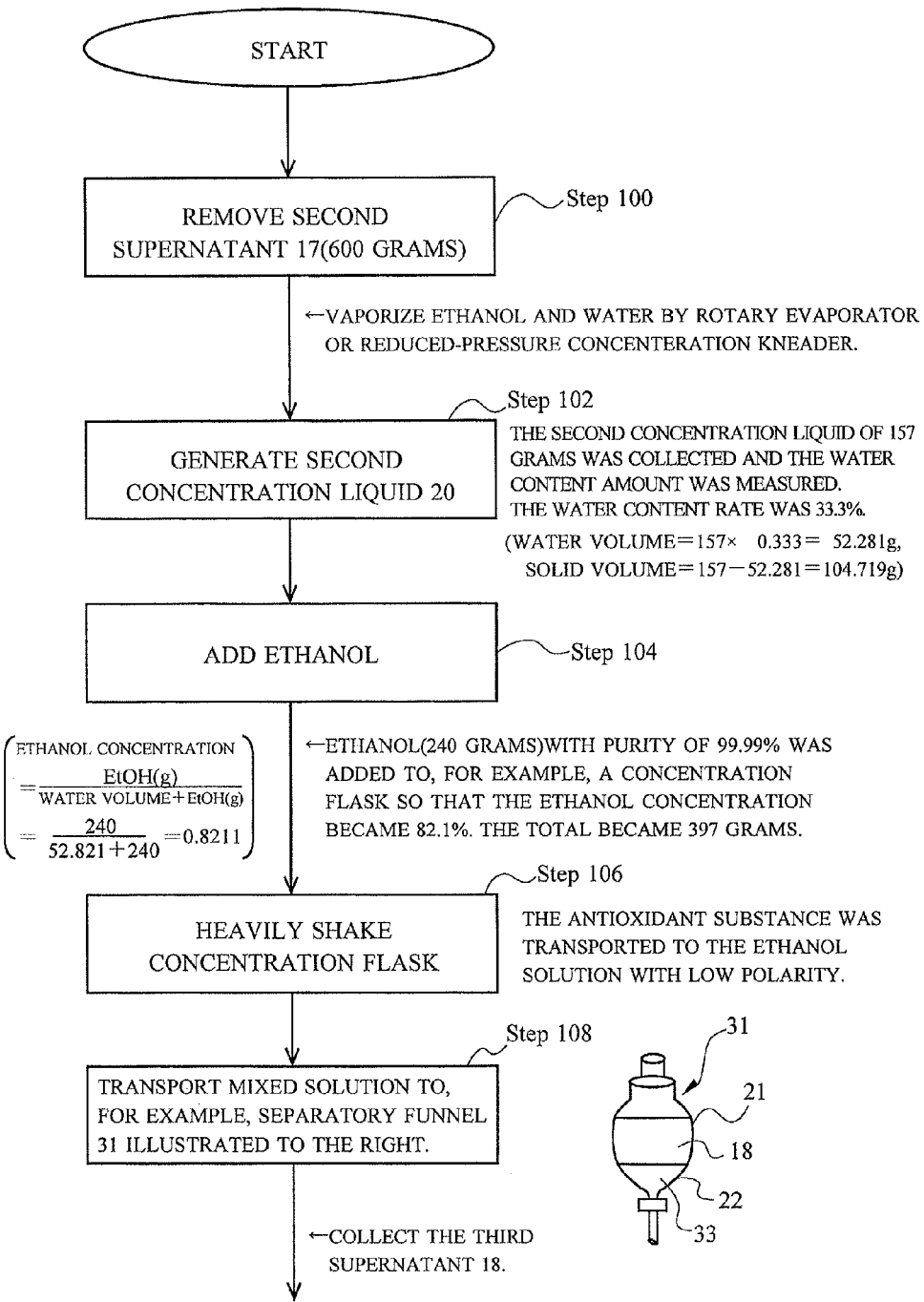
FIG. 9 is a flowchart illustrating the method for producing the oyster meat essence incorporating a large amount of antioxidant substance with a high ORAC value according to the second embodiment of the present invention (first)
FIG. 10 is a flowchart illustrating the method for producing the oyster meat essence incorporating a large amount of antioxidant substance with a high ORAC value according to the second embodiment of the present invention (second)
Figure 10:
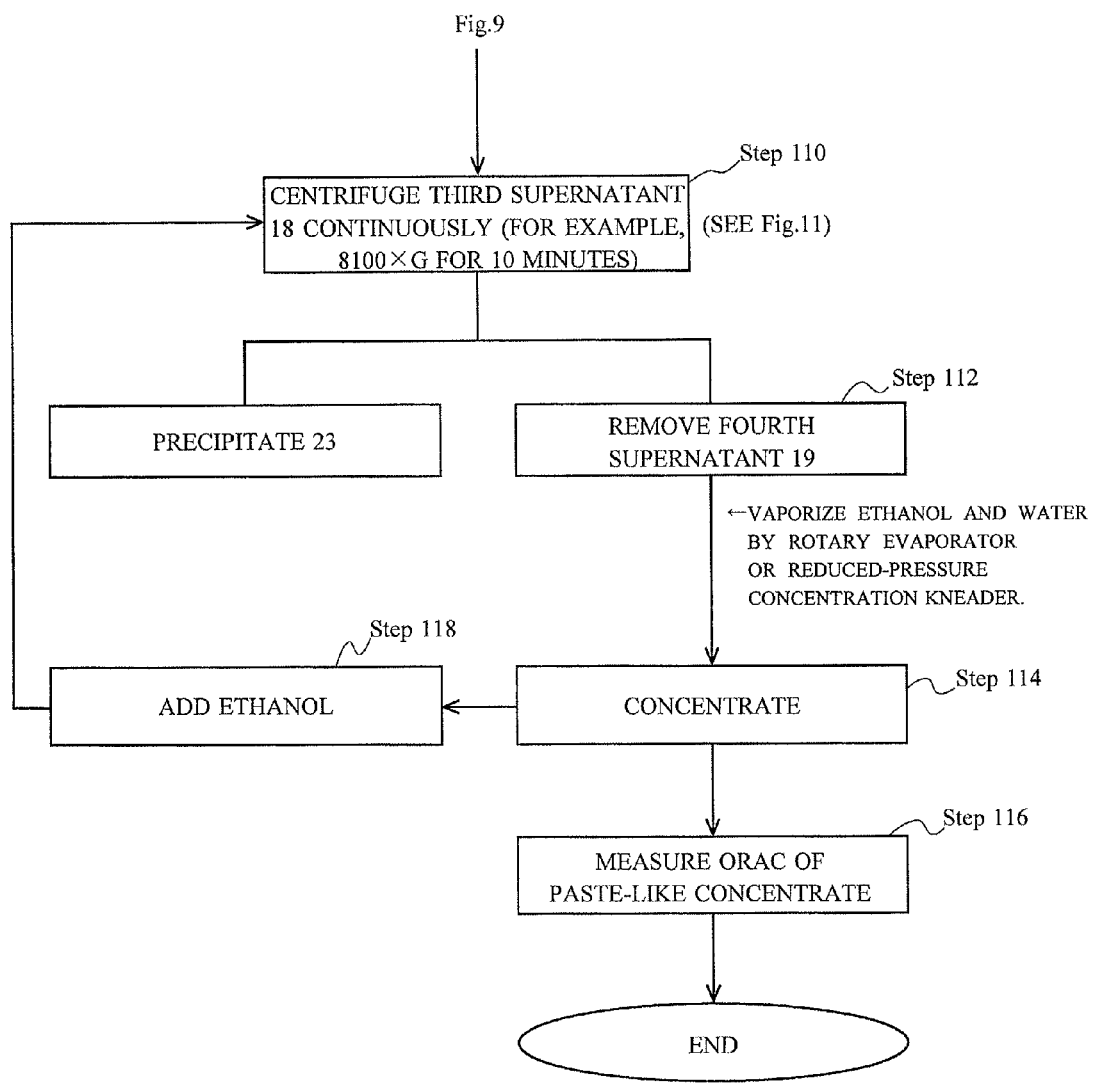

The flowcharts of FIG. 9 and FIG. 10 describe steps of after the second supernatant 17 is removed to the generation of the oyster meat essence including the antioxidant substance with a high ORAC value.

First, the first supernatant 7 is centrifuged (see FIG. 8), and then the precipitate 6 and the second supernatant 17 are separated. Only this second supernatant 17 was removed (Step 100).

The first concentration liquid 4 attenuated to a predetermined ethanol concentration, for example, the ethanol concentration of 70% by adding the ethanol 5 may be constituted as follows. The first concentration liquid 4 is put into the continuous centrifuge from the beginning, continuously centrifuged, and continuously separated into the precipitate 6 and the first supernatant 7 to obtain a large amount of the first supernatant 7.

When the second supernatant 17 obtained as described above was an amount of, for example, 600 grams, this 600 grams of the second supernatant 17 was concentrated and a second concentration liquid 20 was created so as to be a water content rate of approximately 30% (Step 102).

Here, this concentration operation of the second concentration liquid 20 is possibly performed by, for example, a rotary evaporator or a reduced-pressure concentration kneader. However, the concentration operation is not limited to this.

The second concentration liquid 20 was concentrated so as to be the water content rate of approximately 30% and the amount of created second concentration liquid 20 became from 600 grams to approximately 157 grams by the concentration operation. Then, the water content rate was measured. The water content rate was approximately 33.3%.

Here, the ORAC value of the second concentration liquid 20 of 157 grams was measured, and the ORAC value was measured. Even in this step, the ORAC value indicated 290 μmol TE/g: micromoles Trolox-equivalent/gram, which is extremely high value. As described above, the ORAC value of the first supernatant 7 per gram was only 66 μmol TE/g: micromoles Trolox-equivalent/gram.

Next, for example, the ethanol of 240 grams with purity of 99.99% was added so that the ethanol concentration of the second concentration liquid 20 of 157 grams became, for example, approximately 80% as the entire solution. Thus, the ethanol solution with the ethanol concentration of approximately 80% was created.

That is, the ethanol 5 was added to the second concentration liquid 20 with the amount of 157 grams, thus the solution with the amount of 397 grams was created (Step 104).

Then, the solution with the amount of 397 grams, which had ethanol concentration of approximately 80% by adding this ethanol 5, was put into a so-called shaking container (for example, a concentration flask), and the shaking container was heavily shaken (Step 106).

Here, the shaking period and the number of shaking times are not restricted. To shake manually, it is considered that the shaking container is shaken by at least about several tens times, for example, strongly shaken in the vertical direction.

The following is assumed. Heavily shaking the shake container, for example, in the vertical direction promotes transportation of the antioxidant substance with a high antioxidative potency, namely, higher ORAC value to an ethanol solution (relative permittivity: 24) side, which has lower polarity than that of water (relative permittivity: 80). It is considered that transportation and separation of an inhibitor of the antioxidant substance with a high ORAC value to the water side is promoted.

That is, in the shake container, the solution with the ethanol concentration of approximately 80% is clearly separated into an ethanol part 21 with low polarity and a water part 22 with high polarity in the vertical direction.

As illustrated in Step 108 of FIG. 9, for example, the ethanol part 21 with low polarity was transported to the upper part of a separatory funnel 31 while the water part 22, which had higher polarity than that of ethanol, was transported to the lower part of the container. Thus, the ethanol part 21 and the water part 22 were separated. The solution separated to the upper layer had the smaller density and specific gravity compared to the solution at the lower layer. Therefore, the solution moved to the upper layer side and was separated.

Here, a third supernatant 18 separated to the upper layer side became to have 250 grams while a lower layer separate liquid (precipitate) 33 separated at the lower layer side became to have 147 g.

The polarity, density, and specific gravity of the organic solvent will be described. It is considered that there is no proportional relationship between the amount of the polarity, density, and the value of the specific gravity of an organic solvent. Generally, considering with an example of water as a solvent used for extraction, water is a solvent with comparatively high polarity (relative permittivity of 80 as described above: the value of the relative permittivity is regarded as an index whether the polarity is high or low). Meanwhile, an organic solvent that has basically lower polarity than that of water typified by ethanol (relative permittivity: 24) such as alcohol has a smaller density and a specific gravity than that of the water. Accordingly, the organic solvent is transported to the layer upper than that of the water and separated.

That is, in extraction or other processes, a solvent with lower polarity than that of water, for example, ethanol has a smaller density and a specific gravity than those of the solvent at the lower layer (water). Accordingly, the organic solvent is transported to the layer upper than that of the water and is separated.

Whether the polarity is high or low is indicated based on electrical bias in a molecule. The electrical bias of water, to be short, the relative permittivity is 80, which is a large value; therefore, the water is regarded as a solvent with high polarity. As described above, the value of the relative permittivity is regarded as an index of the polarity level.

Here, the third supernatant 18 including the ethanol transferred to the upper layer and separated was concentrated and then formed into a paste. The paste-like third supernatant 18 had a water content rate of 35.2%. It is considered to be preferred that the water content rate be between approximately 40% and approximately 10%.

The ORAC value of the concentrated paste-like third supernatant 18 with the water content rate of 35.2% per gram was measured at 377 μmol TE/g: micromoles Trolox-equivalent/gram, which is an extremely high ORAC value.

In the 377 μmol TE/g: micromoles Trolox-equivalent/gram, the 370 μmol TE/g: micromoles Trolox-equivalent/gram was an ORAC value indicating hydrophilic antioxidative potency while 7 μmol TE/g: micromoles Trolox-equivalent/gram was an ORAC value indicating oleophilic antioxidative potency.

In view of this, it can be inferred that the concentrated paste-like third supernatant 18 with the water content rate of 35.2% incorporates not only a hydrophilic antioxidant substance but also an oleophilic antioxidant substance or an amphiphilic antioxidant substance.

Figure 11:
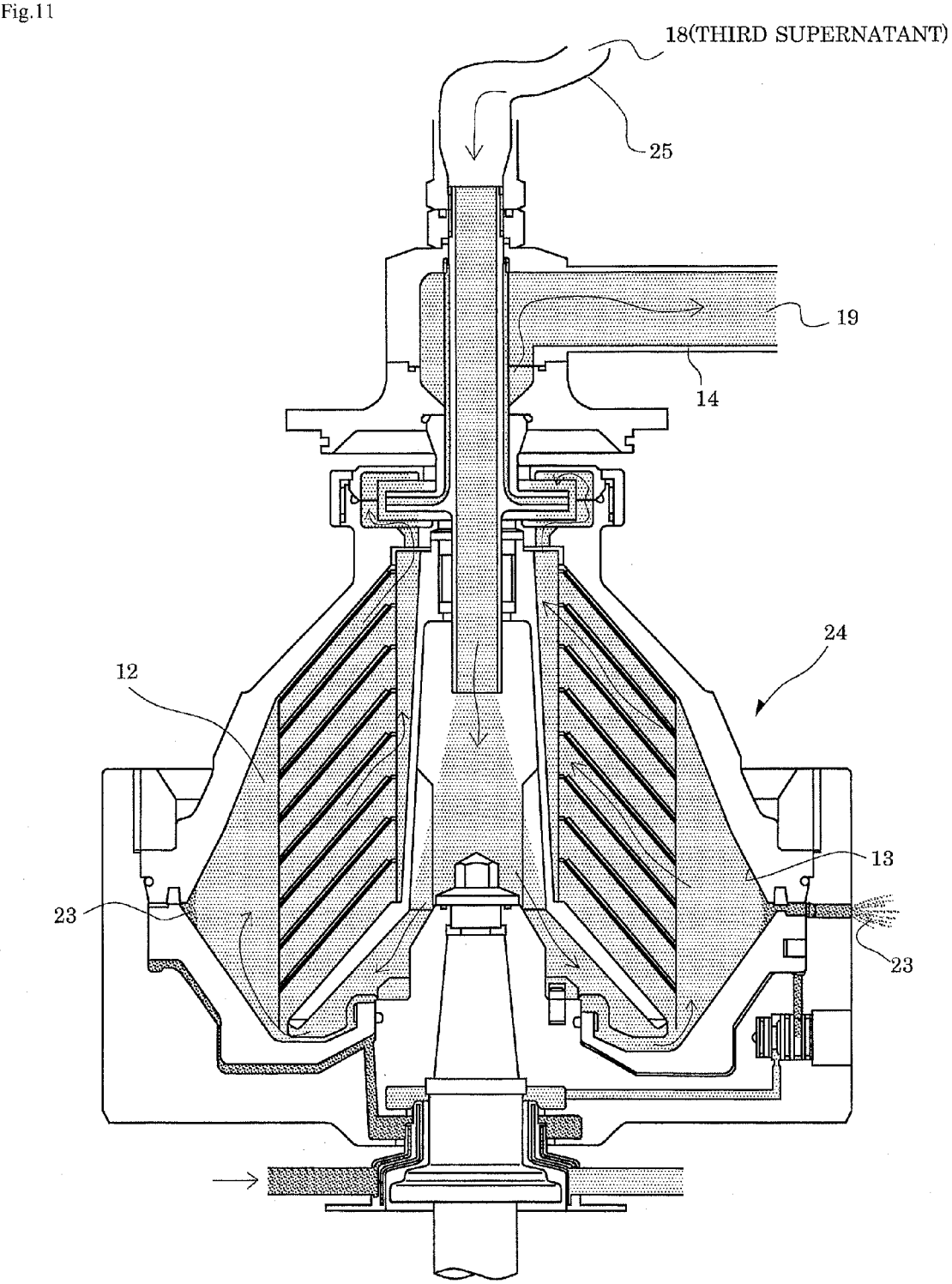
FIG. 11 is an explanatory view illustrating the schematic configuration of the continuous centrifuge according to the second embodiment of the present invention.

As illustrated in FIG. 10, the obtained third supernatant 18 of 250 grams was separated into a fourth supernatant 19 and a precipitate 23 by centrifugation using a continuous centrifuge 24 illustrated in FIG. 11 or similar apparatus (Step 110 and Step 112).

It is considered that this centrifugation operation makes it possible to promote further transporting the antioxidant substance with high antioxidative potency, namely, higher ORAC value, to the second supernatant 19 side. The inhibitor of the antioxidant substance with a high ORAC value can possibly be further transported to the precipitate 23 side, thus facilitating separation.

Next, the fourth supernatant 19 separated and obtained as described above (Step 112) was concentrated by, for example, a rotary evaporator, a reduced-pressure concentration kneader, or similar apparatus (Step 114).

Thus, the concentration liquid of the paste-like fourth supernatant 19 with the water content rate of approximately 34.6% was created. The water content rate at this time is preferred to be in a range of approximately 10% to approximately 40%. The ORAC value of the concentration liquid of the fourth supernatant 19 per gram was measured (Step 116). The ORAC value indicated 389 μmol TE/g: micromoles Trolox-equivalent/gram, which is further extremely high ORAC value.

In the 389 μmol TE/g: micromoles Trolox-equivalent/gram, the 380 μmol TE/g: micromoles Trolox-equivalent/gram was an ORAC value indicating hydrophilic antioxidative potency while 9 μmol TE/g: micromoles Trolox-equivalent/gram was an ORAC value indicating oleophilic antioxidative potency.

In view of this, it can be inferred that the paste-like fourth supernatant 19 with the water content rate of approximately 34.6% incorporates not only a hydrophilic antioxidant substance but also a large amount of oleophilic antioxidant substance or an amphiphilic antioxidant substance.

The centrifugation operation using the centrifuge 24 illustrated in FIG. 11 will be described.

It is constituted, for example, the third supernatant 18 can be continuously injected from an injection pipe 25 of the continuous centrifuge 24 illustrated in FIG. 11 to the continuous centrifuge 24.

Here, the injection of the predetermined amount of the third supernatant 18 in the continuous centrifuge 24 is confirmed, and the continuous centrifuge 24 is operated. Thus, the third supernatant 18 is continuously separated into the so-called the precipitate 23 and the fourth supernatant 19.

As seen from FIG. 11, the so-called precipitate 23 was collected to the outer periphery sidewall 13 side of the storage tank 12 by a centrifugal force. Apart from that, the so-called fourth supernatant 19 was delivered from upward of the storage tank 12 to the outside via the delivery pipe 14.

In the present invention, it was confirmed that the fourth supernatant 19 incorporated not only a hydrophilic antioxidant substance with extremely high antioxidative potency and high ORAC value but also an oleophilic antioxidant substance or an amphiphilic antioxidant substance as described above.

Figure 12:
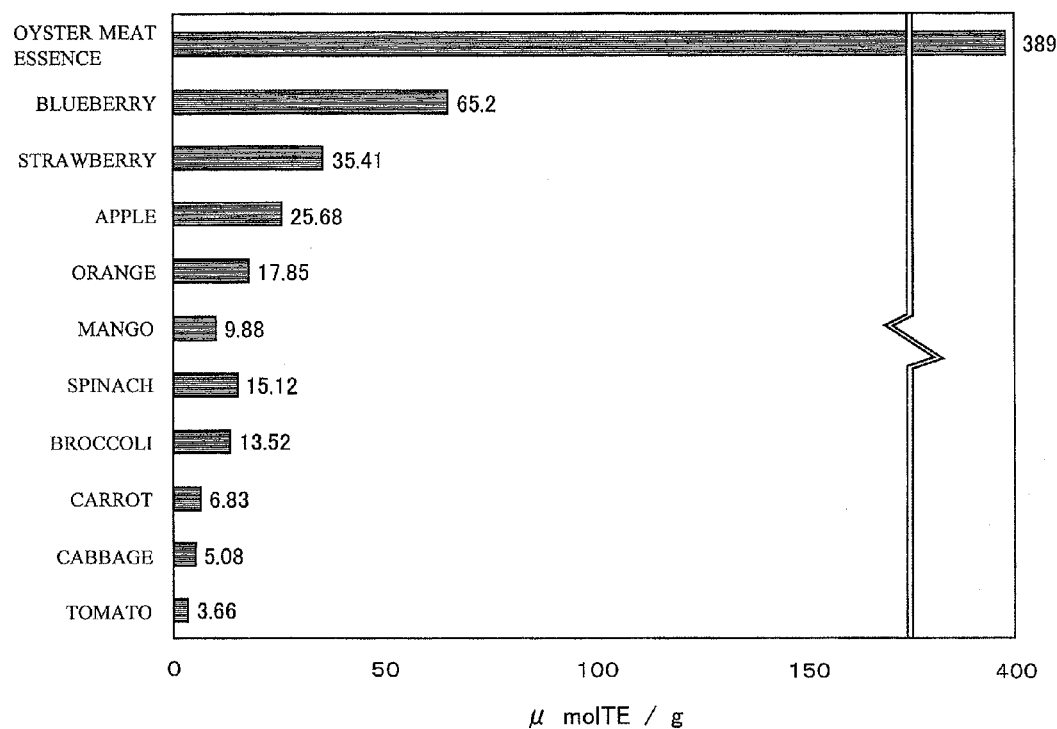
FIG. 12 is an explanatory view illustrating ORAC values of various food products in the second embodiment.

ORAC Company in the United States of America makes a database of ORAC values of various food products as already described. The graph of the ORAC values is illustrated in FIG. 12. As seen from FIG. 6, even a blueberry, which is recognized as having a high ORAC value by ORAC Company in the United States of America, the ORAC value is 66.2 μmole TE/g.

In contrast to this, it can be seen that the paste-like fourth supernatant 19 with the water content rate of approximately 34.6% in this working example incorporates an antioxidant substance with the ORAC value of 389 μmole TE/g: micromoles Trolox-equivalent/gram, which is a value regarded as having high antioxidative potency and ORAC value approximately equal to or more than five times the ORAC value of the blueberry.

Ethanol was added to the fourth supernatant 19 concentrated in Step 114 again (Step 118). The fourth supernatant 19 was repeatedly centrifuged with the continuous centrifuge 24 according to the present invention. The fourth supernatant 19 was allowed to be further separated. An antioxidant substance with further extremely high ORAC value can be collected, for example, in the fifth supernatant or the sixth supernatant concentrated to a paste shape after the separation.

LIST OF REFERENCE SYMBOLS 1 water
2 extraction container
3 oyster meat
4 concentration liquid
5 ethanol
6 precipitate
7 supernatant
8 continuous centrifuge
9 injection pipe
10 left side delivery pipe
11 right side delivery pipe
12 storage tank
13 outer periphery sidewall
14 delivery pipe
15 centrifugation precipitate
16 centrifugation supernatant
17 second supernatant
18 third supernatant
19 fourth supernatant
20 second concentration liquid
21 ethanol part
22 water part
24 continuous centrifuge
25 injection pipe
31 reparatory funnel
33 lower layer separate liquid

The invention claimed is:
1. A method for producing an oyster meat product with high antioxidative potency, comprising:
(a) storing an oyster meat in an extraction container where a water solution is accumulated,
(b) extracting liquid from the oyster meat in the extraction container to generate an extract liquid,
(c) removing the oyster meat from the extraction container after the extracting,
(d) concentrating the extract liquid after the removal of the oyster meat to generate a concentration liquid,
(e) adding ethanol to the concentration liquid,
(f) stirring the concentration liquid to separate the concentration liquid into a precipitate and a first supernatant by a natural sedimentation method,
(g) removing the first supernatant after the separation,
(h) injecting the first supernatant together with the ethanol to a continuous centrifuge,
(i) rotating the continuous centrifuge at a rotation speed which applies a centrifugal acceleration of approximately 8157×g to the first supernatant, wherein the first supernatant is separated into a second supernatant and a centrifugation precipitate,
(j) removing the second supernatant from the continuous centrifuge,
(k) concentrating the second supernatant to obtain a concentrated second supernatant,
(l) adding ethanol to the concentrated second supernatant,
(m) shaking the concentrated second supernatant to separate the concentrated second supernatant into an ethanol layer and an aqueous layer,
(n) removing the ethanol layer to obtain a third supernatant,
(o) concentrating the third supernatant to obtain a concentrated third supernatant,
(p) injecting the concentrated third supernatant to a continuous centrifuge,
(q) rotating the continuous centrifuge at a rotation speed which applies a centrifugal acceleration of approximately 8157×g to the third supernatant, wherein the third supernatant is separated into a fourth supernatant and a centrifugation precipitate,

(r) removing the fourth supernatant from the continuous centrifuge, and
(s) concentrating the fourth supernatant to obtain a concentrated fourth supernatant which is in the form of a paste,
wherein the concentrated fourth supernatant has an ORAC value of at least 160 μmol TE/g, to obtain the oyster meat product with high antioxidative potency.

2. The method according to claim 1, wherein the first supernatant is continuously injected together with the ethanol into the continuous centrifuge.

3. The method according to claim 1, wherein the ethanol is added to the concentration liquid to produce a mixture having an ethanol concentration of 30% to 90%.

* * * * *